US007358039B2

(12) United States Patent
Fischer et al.

(10) Patent No.: US 7,358,039 B2
(45) Date of Patent: *Apr. 15, 2008

(54) FIXED-DRIED RED BLOOD CELLS

(75) Inventors: Thomas H. Fischer, Hillsborough, NC (US); Marjorie S. Read, Durham, NC (US); Arthur P. Bode, Greenville, NC (US); Timothy C. Nichols, Chapel Hill, NC (US)

(73) Assignees: University of North Carolina at Chapel Hill, Chapel Hill, NC (US); East Carolina University, Greenvile, NC (US)

( * ) Notice: Subject to any disclaimer, the term of this patent is extended or adjusted under 35 U.S.C. 154(b) by 370 days.

This patent is subject to a terminal disclaimer.

(21) Appl. No.: 11/041,560

(22) Filed: Jan. 24, 2005

(65) Prior Publication Data

US 2006/0083719 A1   Apr. 20, 2006

Related U.S. Application Data

(62) Division of application No. 10/231,635, filed on Aug. 30, 2002, now Pat. No. 6,884,573.

(60) Provisional application No. 60/316,674, filed on Aug. 31, 2001.

(51) Int. Cl.
  *A01N 1/02*   (2006.01)
  *A01N 63/00*  (2006.01)
(52) U.S. Cl. .......................................... 435/2; 424/93.73
(58) Field of Classification Search ..................... None
  See application file for complete search history.

(56) References Cited

U.S. PATENT DOCUMENTS

| | | | |
|---|---|---|---|
| 3,987,159 A | | 10/1976 | Spona et al. |
| 4,386,069 A | * | 5/1983 | Estep ........................... 424/533 |
| 4,688,387 A | | 8/1987 | Conaway |
| 4,757,052 A | | 7/1988 | Markov |
| 4,774,088 A | | 9/1988 | Vora |
| 4,874,690 A | | 10/1989 | Goodrich, Jr. et al. |
| 5,651,966 A | | 7/1997 | Read et al. |
| 5,891,393 A | | 4/1999 | Read et al. |
| 5,993,804 A | | 11/1999 | Read et al. |
| 6,884,573 B2 | * | 4/2005 | Fischer et al. .................. 435/2 |

OTHER PUBLICATIONS

Labow et al., "The effect of the plasticizer di(2-ethylhexyl)phthalate on red cell deformability", BLOOD 70 (1) : 319-23 (1987).*
AABB Technical Manual, p. 178 (1999).
Armstrong, Jonathan K., et al., Covalent Binding of Poly (Ethylene Glycol) (PEG) to the Surface of Red Blood Cells Inhibits Aggregation and Reduces Low Shear Blood Viscosity, *American Journal of Hematology*, vol. 56, pp. 26-28 (1997).

Ault, Kenneth A., et al., Correlated Measurement of Platelet Release and Aggregation in Whole Blood, *Cytometry*, vol. 10, pp. 448-455 (1989).
Bakaltcheva, Irina, et al., Reversible Cross-Linking and CO Treatment as an Approach in Red Cell Stabilization, *Cryobiology*, vol. 40, pp. 343-359 (2000).
Bode, Arthur P., et al., The Use of Inhibitors of Platelet Activation or Protease Activity in Platelet Concentrates Stored for Transfusion, *Blood Cells*, vol. 18, pp. 361-380 (1992).
Estep, Timothy N, et al., Characterization of Erythrocyte Quality During the Refrigerated Storage of Whole Blood Containing Di-(2-Ethylhexyl) Phthalate, *Blood*, vol. 64, No. 6, pp. 1270-1276 (Dec. 1984).
Fischer, Timothy H., et al., Intracellular function in rehydrated lyophilized platelets, *British Journal of Hematology*, vol. 111, pp. 167-174 (2000).
Goodrich, Raymond P., et al., Preservation of metabolic activity in lyophilized human erythrocytes, *Proc. Natl. Acad. Sci. USA*, vol. 89, pp. 967-971 (1992).
Hortin, Glen L., et al., Progress Toward Preparation of Universal Donor Red Cells, *Art. Cells. Blood Subs., and Immob. Biotech.*, vol. 25, No. 5, pp. 487-491 (1997).
Pietta, P.G., et al., Comparison of the Properties of Human Hemoglobin Covalently Bound to Carboxyl Dextrans with Free and Polymerized Hemoglobin, *Preparative Biochemistry*, vol. 14, No. 4, pp. 313-329 (1984).
Read, Marjorie S., et al., Preservation of hemostatic and structural properties of rehydrated lyophilized platelets: Potential for long-term storage of dried platelets for transfusion, *Proc. Natl. Acad. Sci. USA*, vol. 92, pp. 397-401 (Jan. 1995).
Sano, Wakaba, et al., Beneficial Effect of Fructose-1,6-bisphosphate on Mitochondrial Function During Ischemia-Reperfusion of Rat Liver, *Gastroenterology*, vol. 108, pp. 1785-1792 (1995).
Scott, Mark D., et al., Chemical camouflage of antigenic determinants: Stealth erythrocytes, *Proc. Natl. Acad. Sci. USA*, vol. 94, pp. 7566-7571 (Jul. 1997).
Takeuchi, Koh, et al., Administration of Fructose 1,6-Diphosphate During Early Reperfusion Significantly Improves Recovery of Contractile Function in the Postischemic Heart, *The Journal of Thoracic and Cardiovascular Surgery*, vol. 116, No. 2, pp. 335-343 (Aug. 1998).
International Search Report for International Application Serial No. PCT/US02/27898 dated Dec. 23, 2002.

* cited by examiner

*Primary Examiner*—Sandra E. Saucier
(74) *Attorney, Agent, or Firm*—Myers Bigel Sibley & Sajovec, P.A.

(57) ABSTRACT

Fixed-dried red blood cells (RBCs), and processes for preparing the same are disclosed. The red blood cells, upon reconstitution with distilled water or appropriate buffer: bind oxygen with native affinities, have partial deformability, present minimal thrombogenicity to platelets, and have oblated blood group antigens. The RBCs are preferably fixed by means of cross-linkers with aldehyde functions such as paraformaldehyde or glutaraldehyde either alone or in combination. Native oxygen kinetics are achieved by preparing the red blood cells with 1,6-diphosphofructose. Blood group antigens and chemical functions that render the lyophilized RBCs thrombogenic are occluded by chemically attaching polyoxyethylene glycol polymers to the surface membrane of the red blood cells. The cross-linked red blood cells are preferably died by lyophilization.

9 Claims, 6 Drawing Sheets

Scanning electron microscopy
of lyophilized RBCs demonstrating
normal shape and size
morphology
Upper right panel: comparison of
Native and lyophilized RBCs.

Transmission electron microscopy
of lyophilized RBCs showing normal
ultrastructural morphology

FIGURE 5- OBLATION OF RL RBC SURFACE THROMBOGENICITY

RL RBCs were mixed with fresh platelets as biosensors for foreign surfaces

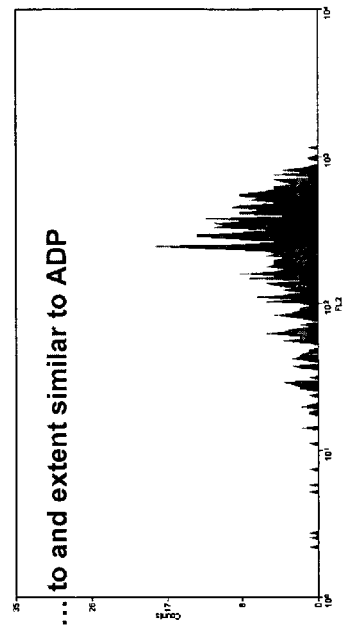
RL RBCs + Platelets
RL RBCs activate platelets...

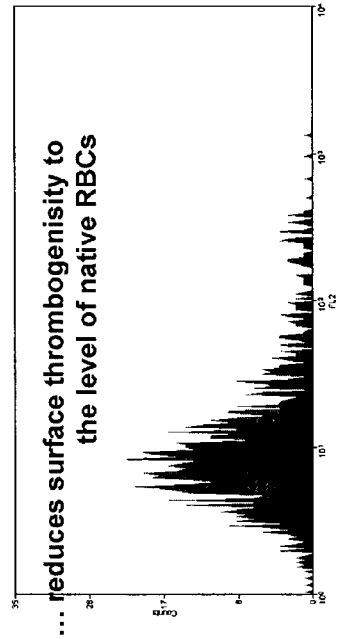
Native RBCs + Platelets + ADP
...to and extent similar to ADP

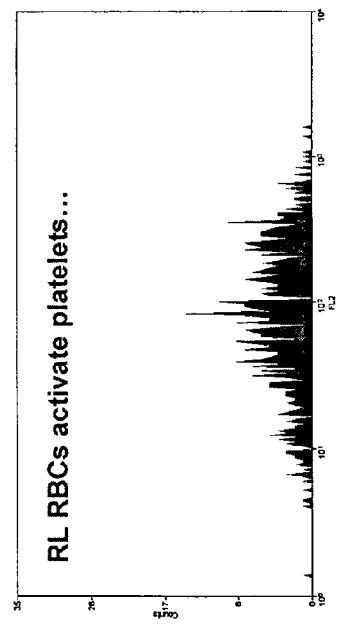
PEG-RL RBCs + Platelets
PEG attachment to RL RBCs...

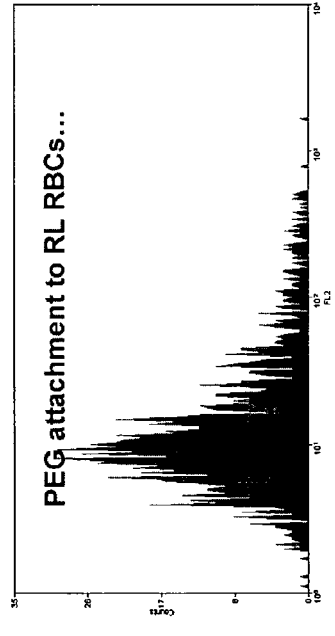
Native RBCs + Platelets
...reduces surface thrombogenisity to the level of native RBCs Platelet p-selectin expression
(anti-CD62p Mab-PE fluorescence)

Events

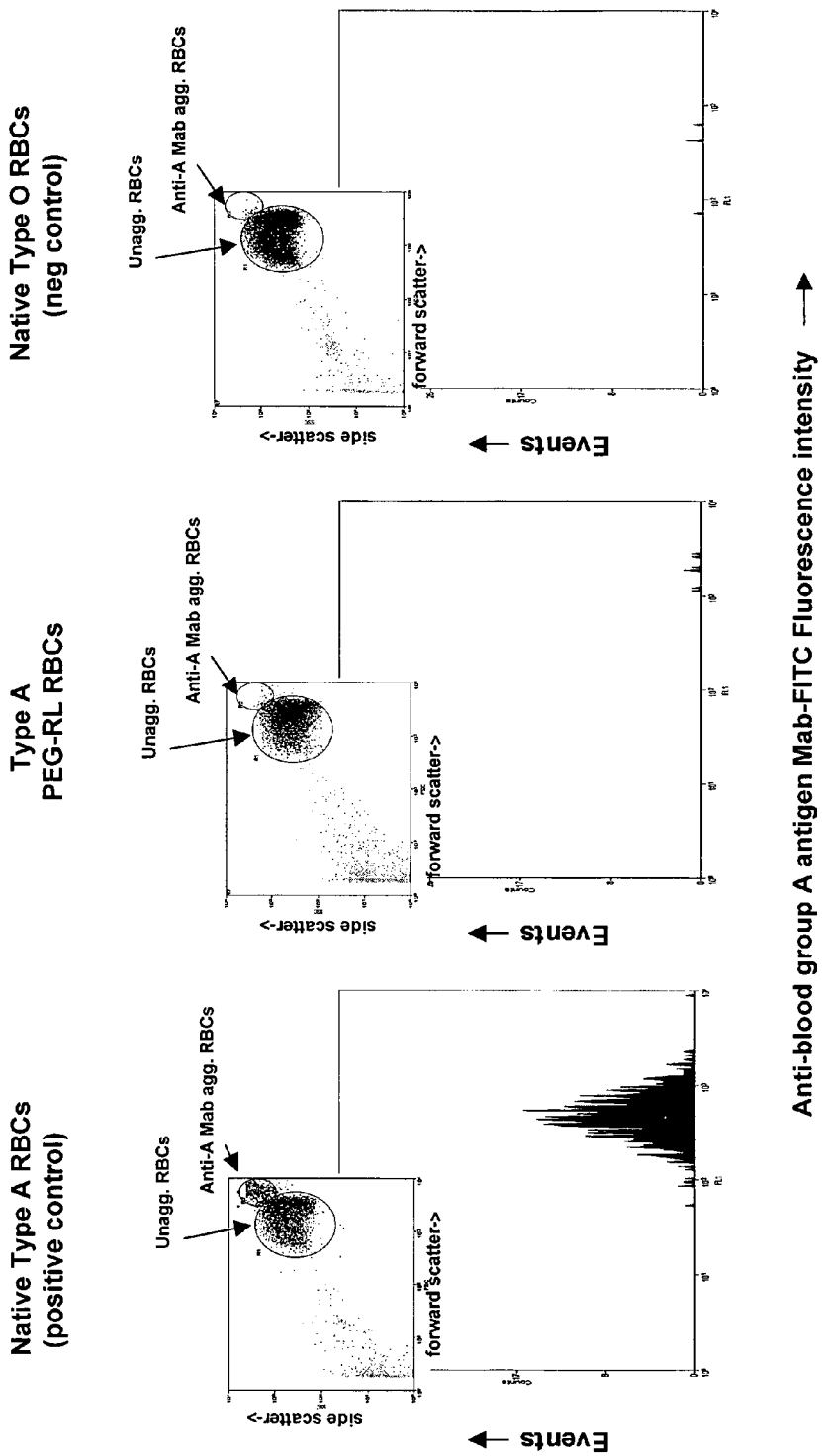
FIGURE 6- OCCLUSION OF RL RBC MEMBRANE BLOOD GROUP A-ANTIGEN
Flow cytometric analysis with anti-blood group A Mab shows that the type A carbohydrates on PEG-RL RBCs are occluded.

FIXED-DRIED RED BLOOD CELLS

CLAIM FOR PRIORITY AND CROSS-REFERENCE TO OTHER APPLICATIONS

This application claims priority to and is a divisional of parent application Ser. No. 10/231,635 filed Aug. 30, 2002, now issued as U.S. Pat. No. 6,884,573, which claims priority to U.S. provisional application No. 60/316,674, filed Aug. 31, 2001, the disclosure of which is hereby incorporated herein by reference.

STATEMENT OF FEDERAL SUPPORT

This invention was made with Government support under grant number N00014-97-1-0867 from the Office of Naval Research. The Government has certain rights to this invention.

FIELD OF THE INVENTION

The present invention relates to methods, based on stabilization of cellular structures with chemical cross-linkers and lyophilizaton, for preparing human and other mammalian species red blood cells for storage for allographic (same species) and xenographic (across species) transfusion for medical purposes.

BACKGROUND OF THE INVENTION

The use of red blood cell (RBC) concentrates for providing oxygen carrying capacity in transfusion medicine is well established for applications that include in the treatment of anemias and hemorrhagic trauma. Red blood cells can be stored for up to 42 days under current AABB guidelines at reduced temperatures as detailed by Menitove, J. eds (1999) Standards for blood banks and transfusion services, 19th ed. Bethesda, Md.: AABB. Technologies have been developed for the cryopreservation of RBCs for long-term storage in the frozen state that require post-thawing steps to remove the RBCs from cryopreservatives before infusion (Vengelen-Tyler, V. eds. (1999) AABB Technical Manual, p. 178 13th ed. Bethesda, Md.: AABB). In order to minimize the logistical complexities of blood banking fresh and cryopreserved RBCs, we have developed methods for preparing lyophilized RBCs with a prolonged shelf-life for infusion after simple rehydration with $H_2O$ or buffer.

Two methods have been described previously for the preparation of lyophilized RBCs. First, Goodrich et al. (Proc. Natl. Acad. Sci. USA (1992) 89, 967-971; U.S. Pat. No. 4,874,690) outline methods for freezing RBCs in the presence of monosaccharides, polyanions and polymers and drying by sublimation of water. Post-hydration processing is required to remove the cryopreserving agents. Secondly, Bakaltcheva et al. (2000) Cryobiology 40, 343-359 describe procedures for stabilizing RBCs with the reversible chemical cross-linker dimethyl 3,3-dithiobispropionimidate and then freezing the cells in the presence of glucose as a cryopreservative with hemoglobin ligated by carbon monoxide. After freeze-drying and lyophilization, the cells are rehydrated and the cross-linker is reversed with dithioerythritol to restore approximately native osmotic fragility and deformability.

SUMMARY OF THE INVENTION

The present invention provides methods for the stabilization of cellular structures with chemical cross-linkers and lyophilizations in the preparation of red blood cells for long-term storage.

Accordingly, a first aspect of the present invention is fixed-dried mammalian red blood cells containing exogeneous fructose 1,6-diphosphate, preferably in an amount effective to enhance the oxygen carrying capacity thereof (e.g., the cells have an oxygen-carrying capacity greater than would the same cells in the absence of exogeneous fructose 1,6-diphosphate).

A second aspect of the present invention comprises fixed-dried mammalian red blood cells having a water-soluble polymer covalently coupled to the cell membrane thereof.

A third aspect of the present invention is a method of making fixed-dried mammalian red blood cells, comprising the steps of providing mammalian red blood cells, cross-linking the red blood cells, then freezing said red blood cells at ambient or elevated pressures sufficient to form ice II, ice III, ice V or ice VI therein; and then drying said frozen cells to produce said fixed dried mammalian red blood cells. Cells produced by the foregoing method are also an aspect of the invention.

A further aspect of the present invention is the use of cells as described above for the preparation of a composition or medicament for administration to a subject to administer red blood cells to the subject.

A further aspect of the present invention is a formulation comprising red blood cells as described above reconstituted in an aqueous carrier solution.

A still further aspect of the present invention is a method of administering red blood cells to a mammalian subject, comprising reconstituting red blood cells as described above in an aqueous carrier solution, and then administering the reconstituted red blood cells to the subject.

The foregoing and other objects and aspects of the present invention are explained in detail in the specification set forth below.

BRIEF DESCRIPTION OF THE DRAWINGS

FIG. 5—Reduction of surface thrombogenicity of lyophilized RBCs with covalent PEG 5,000 attachment.

FIG. 6—Occlusion of blood A antigen with covalent attachment of PEG 5,000.

DETAILED DESCRIPTION OF PREFERRED EMBODIMENTS

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

"Mammalian" as used herein, refers to both human and animal subjects and human and animal blood cells, such as dogs, cats, horses, pigs, cows, rabbits, goats and the like. Thus the present invention may be used in both human medical and veterinary medical applications.

The present method of RBC stabilization with aldehyde-based chemical cross-linkers has been used to prepare lyophilized platelets that retain many aspects of native function (U.S. Pat. No. 5,651,966) It was demonstrated that with mild aldehyde cross-linking, rehydrated, lyophilized (RL) platelets have a near normal ultrastructure by electron microscopy and retain many of the surface membrane functions of fresh platelets (Read et al. (1995) Proc. Natl. Acad. Sci. USA 92:397-401). RL platelets adhere to denuded subendothelium, spread on foreign surfaces (Read et al. (1995) Proc. Natl. Acad. Sci. USA 92:397-401) and the glycoprotein IIb-IIIa and Ib-IX complexes respectively bind fibrinogen (Sanders et al. (1996) Blood 88:S107) and von Willebrand factor (Khandelwal et al. (1997) FASEB J. 11:1812). It was also demonstrated that RL platelets catalyze the conversion of prothrombin to thrombin and (U.S. Pat. No. 5,651,966). Read et al. conducted in vivo experiments in which RL platelets decrease bleeding times in thrombocytopenic rats and participate in thrombus formation in a canine model system (Read et al. (1995) Proc. Natl. Acad. Sci. USA 92:397-401). It was also shown that intracellular stimulus-response signaling was operant in RL platelets (Fischer et al., (2000) Brit. J. Haem. 111, 167-175).

Both the protein kinase C (PKC) and myosin light chain kinase (MLCK) signaling were stimulated in RL platelets in response to activating agents. This finding was important because of the role PKC and MLCK play in orchestrating the aggregation and clot retraction. These results demonstrated that RL platelets are not simply "circulating membranes", but can be activated. The cross-linker was required for preparing lyophilized RBCs and platelets because the transition from the liquid to ice phase state (for the ice I phase) results in an approximately 8% expansion in volume that ruptures membranes and distorts intracellular structures (see, for example, Dahl and Staehelin (1989) J. Electron Micr. Tech. 13:165-174). This invention provides methods for stabilizing the structure of RBCs prior to freezing so as to minimize damage due to ice crystal expansion.

Figure 1:
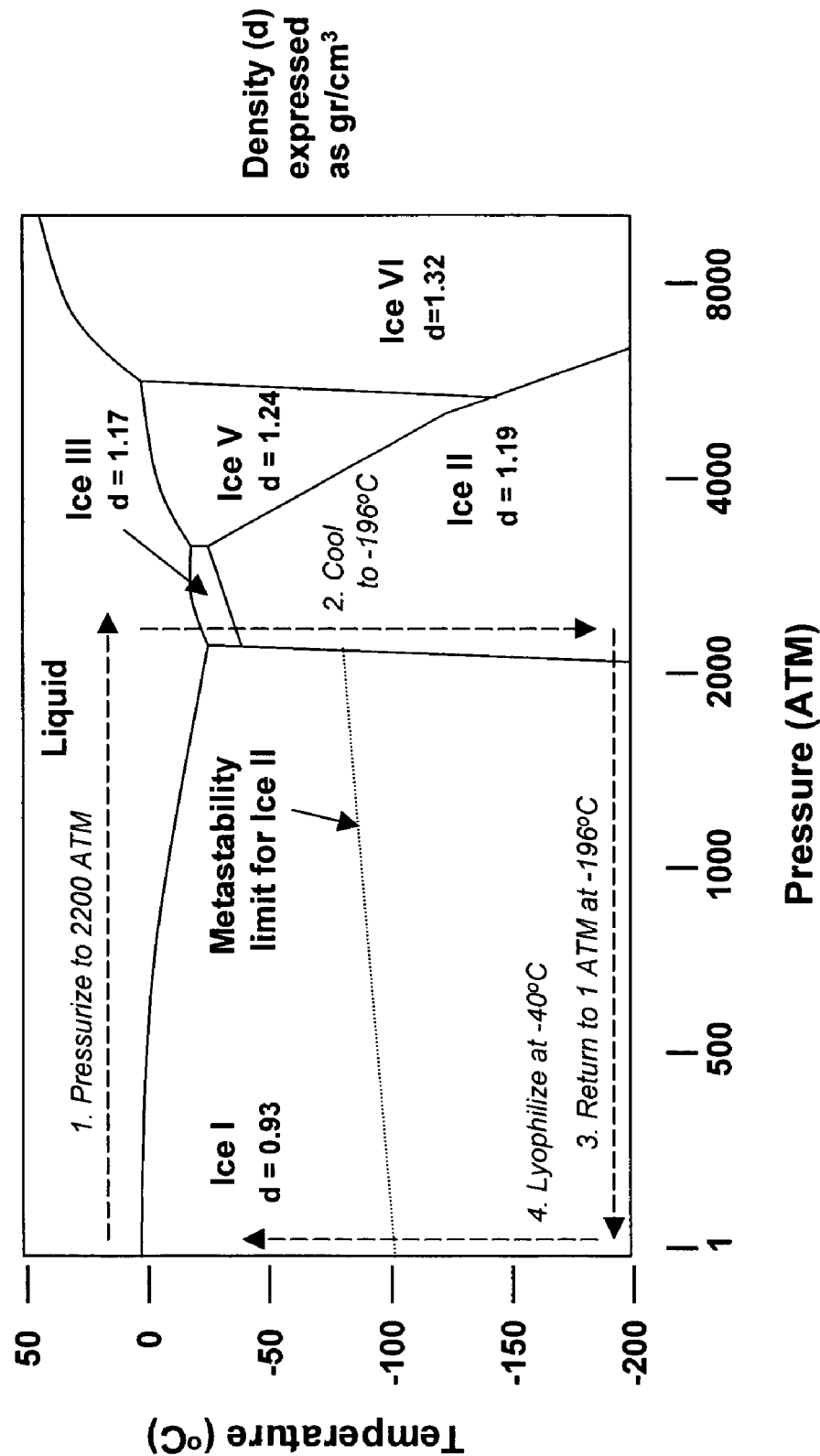
FIG. 1—The trajectory for hyperbaric preparation of rehydrated, lyophilized red blood cells.

An alternative, or complementary, method for minimizing damage from ice crystal expansion is to freeze into and lyophilize RBCs from high pressure phase states of ice. Defined by Bridgman, P., (1935) J. Chem. Phys. 3, 597-603, the high pressure phase states of ice (Ice III, Ice II, Ice IV, Ice V and Ice VI) are denser than water. The ice III and ice III phase states are the lowest pressure forms, with an approximately isothermal transition point at temperatures less than −20° C. and pressures of 2000 atmospheres (Bridgman, P. (1935) J. Chem. Phys. 597-603). The ice II/III phase states are metastable at temperatures below −120° C. (Bertie, J., Calvert, L. and Whalley, E. (1963) J. Chem. Phys. 38, 840; Dowell, L. and Rinfret, A. (1960) Nature 188, 1144) and exert finite vapor pressures for lyophilization (Livesey et al. (1991) J. Microscopy 205-215). Lyophilization from ice II/III phase states have been accomplished through "molecular distillation" methods as described by Livesey et al. (1991) J. Microscopy 205-215. Three lines of evidence indicate that red blood cells can be subjected to and frozen at elevated pressures with retention of viability. First, electron microscopists have noted with many types of mammalian tissues that hyperbaric freezing at the liquid→ice III transition minimizes the extent of structural distortion due to ice I crystallization (see Monaghan, et al. (1998) J. Microscopy 192:248-258 or Dahl and Staehelin (1989) J. Electron Micr. Tech. 13:165-174 for a review). Secondly, barophilic bacteria have been isolated from deep-sea trenches with optimal growth at 700 atm. This result indicates that phospholipid bilayer, chromatin, and other supramolecular structures are stable at 700 atm, and might also retain native functions at higher pressures. Finally, the pressures needed for the formation of ice III, V and VI (see FIG. 1) do not cause wholesale protein denaturation (see Carter, et al. (1971) Cryobiology 8:524-534; Goossens et al. (1996) Eur. J. Biochem. 236:254-262; and Wroblowski et al. (1996) Proteins: Structure, function and genetics 25: 446-55, and for a general review, Silva and Weber (1993) Ann. Rev. Phys. Chem. 44:89-113).

An early realization in the development of hemoglobin-based oxygen carriers was that an effect of covalently cross-linking hemoglobin was to increase the oxygen affinity of the protein out of the physiological range [e.g., Pietta et al., (1984) Pietta, P., Pace, M., Palazzini, G. and Agostoni, A. (1984) Prep. Biochem. 14, 313-329). This affinity increase could be due to modifications of the 2,3-DPG binding site and/or a "locking" of hemoglobin in the high $O_2$ affinity conformation state. We obtained a similar result when RBCs were stabilized for lyophilization by aldehyde cross-linking; oxygen affinity shifted from a normal value of 27 torr to 7 torr. We have shown (Fischer et al. (2000) Blood 94, 2838) that the hemoglobin affinity for oxygen can be directly modulated by preparing RL RBCs with 1,6-diphosphofructose, the upstream source of 2,3-DPG. 1,6-diphosphofructose has previously been used to ameliorate reperfusion injury by providing an anaerobic energy source during ischemia (Takeuchi et al., (1998) J. Thor. and Card. Surg. 116, 335-343; Sano et al., (1995) Gastroenterology 108, 1785-1792). By titrating the RBCs with increasing concentrations of 1,6-diphosphofructose we are able to fine-tune the oxygen affinity hemoglobin in RL RBCs to values between 10 and 50 torr.

Polyoxyethylene glycol (PEG) polymers have been extensively used to sterically occlude theraputic proteins (e.g., Roberts, M. and Harris, M. (1998) J. Pharm. Sci. 87, 1440-1445)) and liposomes (Lasic, D. (1996) Liposomes. Sci. Med. 3, 34-43) from elements of the reticuloendothelial system to prolong circulation times. Several research groups report that the covalent attachement of PEG to the membranes of fresh RBCs so as to occludes blood group antigens (Hortin et al., (1997) Art. Cells, Blood Subs. and Immob. Biotech. 25, 487-491; Scott et al. (1997) Proc. Natl. Acad. Sci. USA 94, 7566-7571; Armstrong et al. (1997) Am J. Hematol. 56, 26-28). We extend this methodology by covalently attaching PEG polymers to the surface membrane of RBCs so as to occlude chemical functions that mediate uptake by the reticuloendothelial system render the lyophilized cells thrombogenic when they contact platelets.

Cross-linked and lyophilized RBCs of the present invention may be prepared with bifunctional cross-linking reagents that are homo or heteromeric with reactive the following reactive moeties: aldehydes, ketones, hydrazides, N-hydroxysulfosuccinimides, N-hydroxysuccinimides, maleimides, imidoesters, active halogens, pyridyl-disulfides, isocyanates, nitrobenzoyloxysuccinimides, nitrobenzenes, imidoesters, photo-activatable azidophenyls and azidopolyaromatics, as well as zero-spacer carbodiimide catalysts. Multi (poly) functional reagents are also considered, as are combinations of two or more cross-linkers, either serially reacted with RBCs for reacted together with RBCs.

RBCs are obtained from mammalian blood with standard phlebotomy, apheresis or exsangination methods according to approved IACCOC protocols. RBCs are freed from plasma platelets, leukocytes and plasma proteins my differential centrifugation, and then treated with chemical cross-linkers. The reaction of the RBCs with the cross-linkers are in general carried out for defined periods of time at temperatures between 20° C. and 37° C. at pre-determined concentration of RBCs. As discussed in greater detail below, care must be taken to sufficiently fix the platelets or undue lysis will be measured upon rehydration of the lyophilized product. The cross-linking step can be carried out in the presence of antioxidants and free-radical scavengers, and the cross-linking reaction can be quenched by adding compounds that contain primary amines. After cross-linking, the RBCs are removed from excess cross-linker and reaction products with differential centrifugation, chromatography and/or dialysis.

Freezing of RBCs after cross-linking may be carried out over a wide range of cooling rates at ambient or hyperbaric pressures. If RBCs (with zero or reduced concentrations of cross-linkers) are frozen into the high-pressure phase states of ice (e.g., ice II/III samples are preferably isothermally pressurized and then isobarically cooled to under −120° C., the point at which ice II/III is metastable (see FIG. 1). RBCs can be frozen in the presence of "stabilizer" small molecules (e.g., glycerol), proteins (e.g., albumin) and polymers (e.g., PEG) which substitute for water in the ice crystal matrix. The perfered "stabilizer" is PEG 8,000 at a final concentration of 1% (w.v). The type and level of "stabilizer" must be infusible as rehydrated. Lyophilization is carried out from temperatures below 0° C., preferably 40° C. if the RBCs were frozen at ambient pressure for ice I, and near or less than −120° C. for molecular distillation from the ice II/III phase states.

Fructose 1,6 diphosphate used to carry out the present invention is known. See, e.g., The Merck Index, Monograph No. 4297 (12$^{th}$ Ed. 1996). 1,6-diphosfofructose is added to RBCs to adjust the oxygen affinity of hemoglobin to defined values, preferably to the common physiological value of 27 torr. 1,6-diphosphofructose is incubated with the RBCs at any step in the isolation and cross-linking procedures, and may be included with "stabilizers" during freezing and lyophilization. 1,6-diphosphofructose is preferably incubated with the RBCs for one hour before and then during a 20 minute cross-linking period at a concentration of 10 mM.

The chemical modification of RBC membranes with cross-linkers imparts a "foreign" nature to the cells with respect to recognition by the reticuloendothelial system and thrombogenic with respect to contact activation of platelets. The surface membrane is thus occluded by covalently attaching polymers that sterically coat the cell membrane. Polymers, particularly water-soluble polymers, that may be used to carry out the present invention are, in general, naturally occurring polymers such as polysaccharides, or synthetic polymers such as polyalkylene oxides such as polyethylene glycols (PEG), polyalkylene glycols, polyoxyethylated polyols, polyvinylpyrrolidone, polyacrylates such as polyhydroxyethyl methacrylate, polyvinyl alcohols, and polyurethane. The polymers may be linear, branched or dendrimeric and may be substituted or unsubstituted. The polymers may, as noted above, be hydrophilic, lipophilic, or both hydrophilic and lipophilic. Polymers are covalently attached through the membrane through reactive chemical functions that include, but are not limited to, aldehydes, ketones, hydrazides, N-hydroxysulfosuccinimides, N-hydroxysuccinimides, maleimides, imidoesters, active halogens, pyridyl-disulfides, isocyanates, nitrobenzoyloxysuccinimides, nitrobenzenes, imidoesters, photo-activatable azidophenyls and azidopolyaromatics, as well as zero-spacer carbodimide catalysts. The preferred polymer is PEG 5,000 with a terminal aldehyde for covalent attachment to surface lysines via Schift's base formation.

In use, the fixed-dried blood cells produced by the procedures described herein are reconstituted (i.e., rehydrated) in an aqueous carrier solution to provide a formulation which is then administered to the subject (for xenographic or allographic infusion). The carrier solution is, in general, a physiologically acceptable carrier solution, such as sterile physiological saline solution. Generally the reconstituted preparation will contain from 1 or 2 up to 6, 8 or $10 \times 10^9$ cells per milliliter. Rehydrated RBC of the invention may any disorder or condition for which the administration of blood cells is beneficial, including but not limited to anemias and as a component of replacement fluids in hemorrhage.

In some embodiments of the invention, it is beneficial to perform certain pre-treatments of the whole blood to improve the quality of the freeze-dried product, as set forth below.

(a). Heat-shock of the whole blood may be used to induce activation of chaperone proteins to reduce protein denaturation during dehydration. This process involves, for example, heating the whole blood in a PL-146 plastic bag at 42 C for 10-15 minutes, preferably in a temperature-controlled water bath, before beginning the washing or cell separation steps. This treatment has been applied to whole tissues and platelet suspensions for improved preservation in room temperature or cold storage, but has not been reported for treatment of red blood cells in preparation for freeze-drying. (See, e.g., A E and Gabai V L; Heat Shock Proteins and Cytoprotection: ATP-Deprived Mammalian Cells, Chapman and Hall (1997)).

(b). Leukodepletion of the whole blood may be carried out by means of commercially available affinity filters. This process involves, for example, passing the whole blood (after heat shock treatment if performed) into the input port of a Pall Purecell Neo leukoreduction filter (or other FDA-approved filter for the purpose of adsorbing white blood cells out of the whole blood) and collecting the effluent in a clean closed container. The benefit from reduction of the white blood cell count at the start is that there will be less possibility of degradation of red cells during further processing by enzymes or oxygen radicals released from activated leukocytes. The most often cited reason in support of leukoreduction for banked blood components is to prevent Graft-verus-Host disease from transfusion in the recipient patient, and the effects on the stored cells has not been adequately investigated. The leukoreduction step may also be performed on the packed red cell mass retained after centrifugation separation of the whole blood into red cells and platelet-rich plasma. See, e.g., Beugeling T, Feijen J, and van Aken W G: "The Mechanisms of Leukocyte Removal by Filtration." in *Transfusion Medicine Reviews*, Vol IX (No. 2): pp 145-166 (1995).

(c). Compounds may be added to the whole blood to, among other things, reduce activation of enzymes in the coagulation, fibrinolytic, or complement system pathways. The primary example of the instant invention mentions a citrate-based anticoagulant based on standard formulae used in blood banking. This formula may be supplemented with addition of, for example, general protease inhibitors (e.g., leupeptin, aprotinin, ethylenediaminetetraacetic acid [EDTA], N-ethyl maleimide, etc), or specific thrombin inhibitors (e.g., hirudin, heparin, Thromstop, etc), or complement convertase inhibitors (e.g. FUT-175, etc), or specific plasmin inhibitors (e.g., e-amino caproic acid, tranexamic acid, etc). These compounds have been applied to various degrees in attempts to improve the storage of platelets for blood banking, but this has not been reported for applications in improving the storage of red blood cells. See, e.g., Bode, A. P., and Norris, H. T.; "The Use of Inhibitors of Platelet Activation of Protease Activity in Platelet Concentrates Stored for Transfusion." *Blood Cells* 18: pp. 361-380 (1992).

Some important embodiments of the instant invention include deliberate incorporation of a plasticizer into the membrane of the fixed red blood cell before dehydration in an amount sufficient to enhance or retain cell deformability at the time of subsequent reconstitution. A preferred embodiment of this feature is performed by suspending the fixed, washed red blood cells prior to freezing in a phosphate buffer containing at least 0.1% bovine serum albumin [BSA] at a cell count of $2-3 \times 10^9$/mL in a PL-146 storage bag held at 4 C and then introducing $\frac{1}{1000}^{th}$ volume of a solution comprised of 20-40 milligrams/mL diethylhexylphthalate [DEHP] dissolved in absolute ethanol or dimethylsulfoxide [DMSO]. The incubation period at 4° C. of the red cells in this solution should be between 48 hours as a minimum and 120 hours as a maximum. At the end of this incubation the red cells should be packed by centrifugation and resuspended in the bulking solutions already described and then taken to freeze-drying. Solutions containing plasticizers such as DEHP have been reported in the literature to impart extra stability to liquid-stored red blood cells in blood bank storage, but this has not been similarly reported for application to a freeze-drying process. See, e.g., Estep T N, Pedersen R A, Miller T J, Stupar K R: "Characterization of erythrocyte quality during the refrigerated storage of whole blood containing Di-(2-ethylhexyl)Phthalate." Blood 64(6): pp. 1270-1276 (1984).

We have found that most of the washing and fixation steps for a larger-scale red cell preparation can advantageously be performed in a closed system by utilizing an appliance called the IBM 2991 Cell Washer, which was originally designed for blood banks to facilitate washing of frozen red cell units to remove cryoprotectant agents like DMSO or glycerol just prior to transfusion. The advantage to employing this device for our purposes in preparing freeze-dried red blood cells is that it provides an aseptic environment for the multiple steps of washing and fixation which would otherwise require handling of the red cells in an open container, and the Cell Washer induces less shear stress to resuspend the packed red cells after each step than would be experienced with a resuspension method by hand. As an example, we introduce into the Cell Washer processing bag a volume of 150-200 mL of a suspension of leukodepleted red blood cells at a cell count of $3-4 \times 10^9$/mL and attach the tubing harness as described in the operating instructions. Then we introduce a volume of 200-250 mL phosphate washing buffer containing 0.1% BSA sterily through the tubing harness and perform wash cycle #1. At the end of the agitation and spinning period programmed into the 2991, the supernatant washing fluid is automatically expressed out to waste and fresh buffer is introduced thru the harness for a total of three washes. After the spinning step of the third wash, a fixation solution containing 0.05% glutaraldehyde in Hank's buffered salt solution [HBSS] is introduced for a timed incubation of 20 minutes at room temperature before spinning, and then three more washing steps are performed with the phosphate buffer. At this point the fixed, washed red cell suspension is removed from the 2991 processing bag and handled in vials and bottles for the bulking and freeze-drying steps.

Combination preparations. Combination products provided herein comprise mammalian red blood cells in combination with mammalian blood platelets. The red blood cells and blood platelets may be provided together as a single composition, or provided in separate containers in the form of a kit or set, as explained further below. In either case, the compositions, kits or sets may be used to prepare a reconstituted blood cell preparation for use in treating subjects as described above for the same reasons as discussed above, such as for trauma or surgery.

Thus, a further aspect of the present invention is a composition of fixed-dried mammalian blood cells, the composition comprising, consisting of or consisting essentially of fixed-dried mammalian red blood cells in combination with fixed-dried mammalian blood platelets. In a preferred embodiment, the ratio by weight of red blood cells to blood platelets in the composition is between 1:0.5 or 1:1, up to about and 3:1 (i.e., permitting relatively more of the RBCs than platelets). Thus the present invention provides a method of administering blood cells to a mammalian subject, comprising reconstituting such a blood cell composition in an aqueous carrier solution (as discussed below) to produce a reconstituted blood cell preparation, and then administering the reconstituted blood cell preparation to the subject Preferably, the reconstituted blood cell preparation containing from 1 or 2 up to 6, 8 or $10 \times 10^9$ red blood cells per milliliter, and from 1 or 2 up to 6, 8 or $10 \times 10^9$ blood platelets per milliliter.

It can be disadvantageous to reconstitute the red blood cells and the blood platelets together due to the heterotypic nature of the cells and cell membranes. A solution to this problem is to reconstitute the different cells separately and then combine the two separate preparations into a single preparation for administration. Hence, a further aspect of the present invention is a kit or set comprising a first container having a composition comprising, consisting of or consisting essentially of fixed-dried mammalian blood cells therein and a second container having a composition comprising, consisting of or consisting essentially of fixed-dried mammalian blood platelets therein. In one embodiment, the ratio by weight of red blood cells to blood platelets in the kit is between 1:0.5 or 1:1, up to 3:1. The components of the kit or set may be packaged together in a common package, and may include (in or on the package) printed instructions for carrying out the methods of use of the kit as described below. Note that the red blood cells and blood platelets may be used together as described below, or separately, depending upon the needs of the particular subject. The kit or set may further contain or include a third container having an aqueous carrier/buffer solution for reconstituting both the red blood cells and the blood platelets (it being preferred but not essential that the same carrier solution be used for reconstituting both the platelets and the RBCs). Such a solution is one which is physiologically acceptable and in general will be sterile, preferably pyrogen-free, and will preferably have a pH of from about 6.5 to 7.5 or 7.8. A method of administering blood cells to a mammalian subject with such a kit or set is generally carried out by reconstituting red blood cells as above in an aqueous carrier solution to form a reconstituted red blood cell preparation; separately reconstituting blood platelets as described herein in an aqueous carrier solution to form an reconstituted platelet preparation;

combining the reconstituted red blood cell preparation with the reconstituted platelet preparation to produce a reconstituted blood cell preparation; and then administering the reconstituted blood cell preparation to the subject. In general, the reconstituted blood cell preparation containing from 1 or 2 up to 6, 8 or $10 \times 10^9$ red blood cells per milliliter and from 1 or 2 up to 6, 8 or $10 \times 10^9$ blood platelets per milliliter.

In the combination methods, products, kits and sets described herein, the red blood cells and platelets may be from the same or different species, but are preferably from the same species. When from the same species, the red blood cells and the platelets may be of the same or different blood type, or may be from the same or different donor. The red blood cells and the platelets may be fixed-dried together, or may be fixed-dried separately and then combined. The platelets may be fixed-dried according to the procedures set forth in U.S. Pat. No. 5,993,804 to Read et al., U.S. Pat. No. 5,891,393 to Read et al., or U.S. Pat. No. 5,651,966 to Read et al. (the disclosures of all patent references cited herein are specifically intended to be incorporated by reference herein in their entirety). In a preferred embodiment, the platelets are characterized in that, upon reconstitution, they (a) adhere to thrombogenic surfaces; (b) do not adhere to non-thrombogenic surfaces; (c) undergo shape change upon adhering to a thrombogenic surface; (d) adhere to one another to form a hemostatic plug upon adhering to a thrombogenic surface; and (e) release their granular contents.

The examples, which follow, are set forth to illustrate the present invention, and are not to be construed as limiting thereof. In the following examples, atm means atmosphere, mm means millimeter, µL means microliter, msec means millisecond, mL means milliliter, mM means millimolar, M means Molar, kDa means kilodalton, and temperatures are defined in degrees Celsius.

EXAMPLE 1

Preparation of Human Lyophilized RBCs with 0.05% Glutaraldehyde (Protocol 1)

Figure 2:
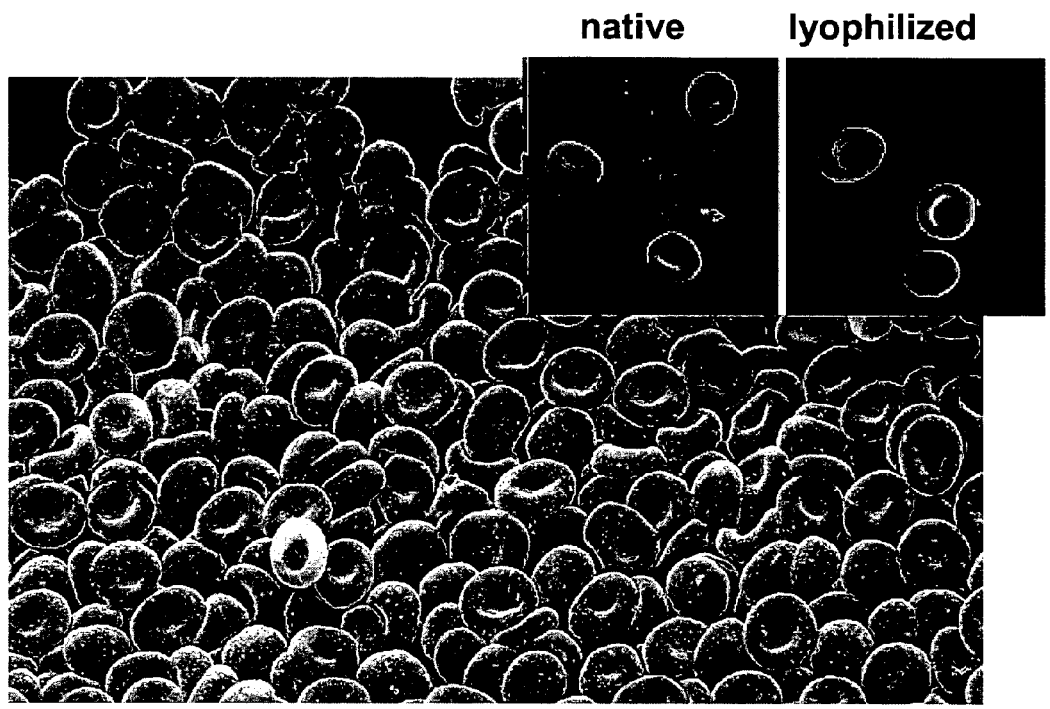
FIG. 2—The normal size and shape morphology of rehydrated RBCs as imaged with scanning electron microscopy for cells prepared as detailed in example 1.
Figure 3:
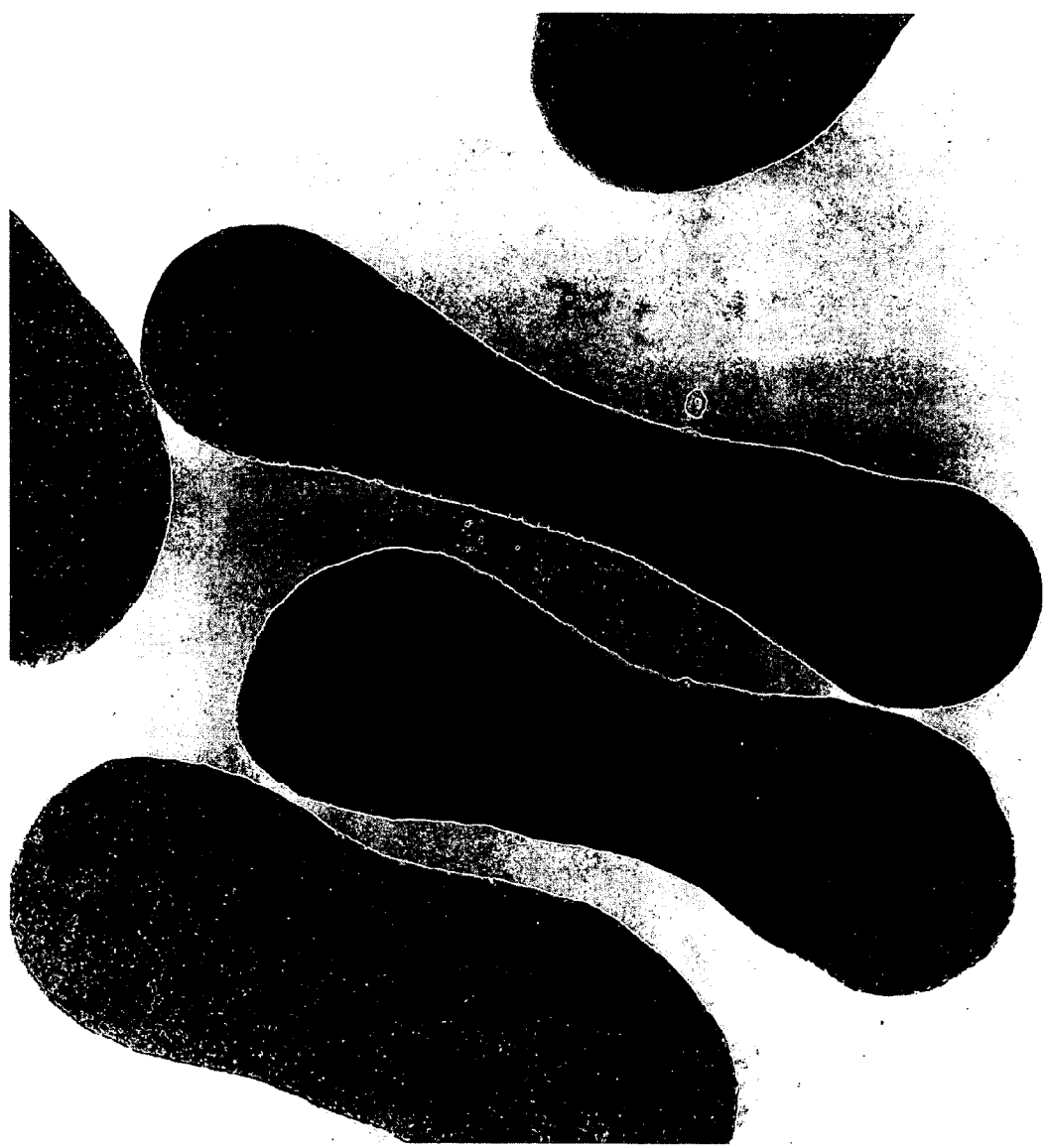
FIG. 3—The normal ultrastructural morphology of rehydrated RBCs as imaged with transmission electron microscopy for cells prepared as detailed in example 1.

4.5 ml of human blood is drawn into a syringe with 0.5 ml CDPA-1. The blood is then gently place into 15 ml conical centrifuge tube and centrifuge for 10 min at 1200 rpm. The upper platelet-rich plasma layer is removed and discarded. RBCs are diluted to a Crit=5% with PBS and centrifuged as before. The supernatant is removed and the RBCs are resuspended in the original volume of PBS for Crit=5%. The centrifugation is repeated and the final pellet is resuspended for a Crit=5% in PBS. Dilute 50% (v/v) freshly opened glutaraldehyde 1/1000 into the RBCs for a final concentration of cross-linker=0.05% (v/v) and incubate for 20 min at 37° C. on rocker. The RBCs are centrifuged as before and the pellet is re suspended for a Crit=5%. The centrifugation is repeated. The final pellet is Resuspended in PBS+1% PEG 8,000 for a Crit=25%. The cross-linded RBCs are proportioned into 2 ml plastic cryovials (no more than 200 ul per vial) or 20 ml glass vials (no more than 1 ml per vial) and frozen by placein in a −80° C. freezer. The cells are lyophilized on a cold stage at −40° C. After lyophilization, the RBCs are stored at −20° C. for up to one year. The lyophilized RBCs are rehydrated by the original freezing volume of sterile $H_2O$. Examination of the cells with scanning (FIG. 2) and transmission (FIG. 3) electron microscopy revealed native morphology.

The level of lysis and hemoglobin release was measured after rehydration by centrifuging the RBCs and measuring the absorbance of hemoglobin in the supernatant at 540 nm. Lyophilized RBCs prepared as detailed in Example 1 were compared to uncross-linked RBCs that were frozen and lyophilized and to freshly isolated (with differential centrifugation) RBCs were centrifuged. The data in Table 1 shows that lyophilized RBCs prepared as in Example 1 were essentially stable to lysis when rehydrated.

TABLE 1

EXTENT OF HEMOLYSIS OF LYOPHILIZED RBCS IN EXAMPLE 1

| RBC Preparation | Percent Hemolysis |
|---|---|
| 0.05% glutaraldehyde fixed (Example 1) | 0.5% |
| 0.00% glutaraldehyde fixed | 100% |
| Fresh cells | 0.3% |

EXAMPLE 2

Preparation of Human Lyophilized RBCs with 1,6-diphosphofructose to Normalize Hemoglobin Oxygen Affinity (Protocol 2)

Figure 4:
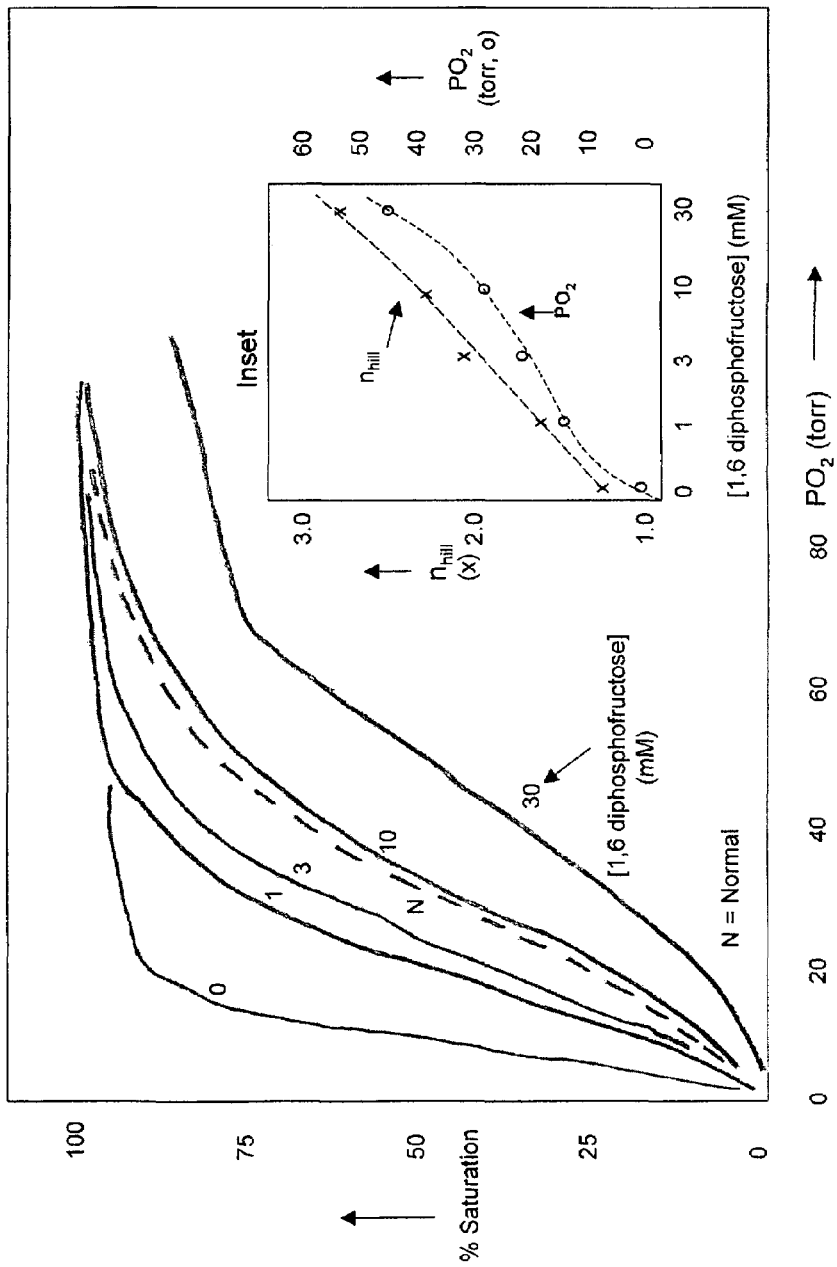
FIG. 4—Titration of hemoglobin oxygen affinity with 1,6-diphosphofructose as described in example 2.

The procedure in example 1 was altered by incubating the centrifically washed RBCs with increasing concentrations of 1,6-diphosphofructose for one hour at room temperature on a rocker before adding the cross-linker, and then for an additional 20 minutes during the cross-linking step. After lyophilization and rehydration, oxygen association-disassociation curves were measured (see FIG. 4). 10 mM 1,6-diphophofructose is the preferred concentration to restore native oxygen ligation kinetics.

EXAMPLE 3

Occlusion of Surface Membrane by Covalent PEG 5,000 Attachment (Protocol 3)

PEG-aldehyde was prepared by dropwise adding 5 ml of 50% (w/v) PEG-amine (MW=5,000) in PBS to 5 ml of 50% (v/v; 6.29 Molar) glutaraldehyde. The resulting solution was dialyzed thee times over a three day period vs. sodium acetate/acetic acid at pH=5.5 with a total acetate/acetic acid concentration of 20 mM. The resulting PEG-aldehyde (5 mM PEG-aldehyde) was stored at 4° C. until use (within four weeks). Immediately before use, the 5 mM PEG-aldehyde stock was diluted 1/1 with 2×PBS.

Human blood was obtained and then RBCs were isolated and freed from plasma proteins with two centrifugational wash steps as detailed in Example 1. The RBCs were suspended in PEG-aldehyde (2.5 mM as prepared above) for a Crit=5% after the last wash and reacted for one hour on a rocker at room temperature. Glutaraldehyde was added to the mixture and allowed to react as described in Example 1. The PEGylated RBCs were freed of reaction byproducts, lyophilized and rehydrated for analysis as outlined in Example 1.

The thrombogenicity of RL RBC preparations was analyzed by incubating the lyophilized cells with human platelets, and then measuring the resulting degree of platelet activation by quantifying p-selectin presentation of the platelet surface membrane with flow cytometry. PEG-modified RL RBCs, unmodified RL RBCs and native RBCs was compared by mixed with human platelet (11 ul) were added to fresh human platelet-rich plasma (1 ul) and incubated 15 minutes at room temperature. The platelets were then labeled by adding 20 ul of anti-CD-61-Per CP conjugate (non-activation dependend) to identify platelets plus 20 ul anti-p-selectin-PE conjugate (to identify activated platelets). Samples were quenched and flow cytometry was performed as detailed by Ault et al (1989) Correlated measurement of platelet release and aggregation in whole blood. Cytometry 10, 448-455. A comparison of panels A and B of FIG. 5 shows that unmodified RL RBCs partially activated platelets; p-selectin was exposed to an extent approaching that measured with ADP activated platelets. In contrast, pegylated RL RBCs (panel C, FIG. 5) did not expose P-selectin beyond the extent of resting platelets (panel D, in FIG. 5).

In addition to the oblation of the surface thrombogenicity of RL RBCs, the covalent attachment of PEG to the lyophilized cells occludes blood group antigen A. PEG-modified RL RBCs were prepared from blood group A RBCs as outlined above in this sample. The occlusion of the blood group antigen was then followed by measuring the reactivity of the RBCs with anti-blood group A monoclonal antibody with flow cytometry. 20 ul of type A PEG-modified RL RBCs, fresh type A RBCs and fresh type O RBCs were reacted with 20 ul of anti-blood group A-FITC conjugated monoclonal antibody (Immunocor) for 20 min at room temp. Samples were quenched and subjected to flow cytometric analysis as detailed by Ault et al (1989) Correlated measurement of platelet release and aggregation in whole blood. Cytometry 10, 448-455. A comparison of the middle and left panel of FIG. 6 demonstrates that covalent attachment of PEG to the surface of RL RBCs effectively occludes the type A antigen.

EXAMPLE 4

Preparation of Lyophilized Human RBCs with Dual Paraformaldehyde and Glutaraldehyde Cross-linkers for Increased Deformability (Protocol 4)

Rehydrated, lyophilized RBCs with enhanced deformabilities were prepared by cross-linking the cells with a dual system of paraformaldehyde and glutaraldehyde. Human RBCs were isolated and prepared for cross-linking as described in Example 1. Instead of a 20 minute reaction with 0.05% glutaraldehyde, the RBCs were reacted first for 30 minutes with paraformaldehyde at a concentration of 0.05% (w/v). At this point, glutaraldehyde was added to the mixture for a final concentration of 0.05% (v/v). After an additional 20 minute incubation with both aldehydes, the RBCs were freed of byproducts, lyophilized and rehydrated as detailed in Example 1. When prepared in this manner, 75% of the cells were capable of transiting a 3 micron pore size filter.

TABLE 2

FILTERABLITY OF LYOPHILIZED RBCs IN EXAMPLE 4[1]

| RBC preparation | % recovery in filtrate |
|---|---|
| 0.01% para, 0.01% glut. RL RBCs | 75% |
| Fresh RBCs | 98% |

[1]Fresh and RL RBCs were prepared for a Crit = 1% in PBS, then 1.0 ml was filtered through a 3.0 micron Millopore Isopore ™ filter with a surface area of 1.33 cm².

EXAMPLE 5

Preparation of Lyophilized Canine and Porcine RBCs with 0.05% Glutaraldehyde (Protocol 5)

Porcine and canine blood was isolated via venipuncture and then RBCs were isolated from other blood cells and plasma proteins as detailed for human RBCs in Example 1. Cross-linking, lyophilizing and rehydration steps were also carried out as described in Example 1. These procedures resulted in lyophilized canine and porcine RBCs that minimally hemolysed upon rehydration.

TABLE 3

EXTENT OF HEMOLYSIS OF LYOPHILIZED RBCS IN EXAMPLE 5

| RBC Preparation | Percent Hemolysis |
|---|---|
| Porcine RL RBCs (Example 5) | 3.7% |
| Canine RL RBCs (Example 5) | 1.2% |
| Fresh porcine RBCs | 100% |
| Fresh canine RBCs | 100% |

The foregoing examples are illustrative of the present invention, and are not to be construed as limiting thereof. The invention is described by the following claims, with equivalents of the claims to be included therein.

What is claimed is:

1. Fixed-dried mammalian red blood cells having a cell membrane, said cell membrane including a plasticizer in an amount sufficient to enhance or retain cell deformability at the time of subsequent reconstitution and containing exogeneous fructose 1,6-diphosphate in an amount effective to enhance the oxygen carrying capacity thereof.

2. The fixed-dried mammalian red blood cells according to claim 1, wherein said blood cells are human red blood cells.

3. The fixed-dried mammalian red blood cells according to claim 1, wherein said blood cells are selected from the group consisting of dog, cat, horse, rabbit and goat red blood cells.

4. The fixed-dried mammalian blood cells according to claim 1, produced by a process comprising:
providing fixed mammalian red blood cells, then
incubating said fixed mammalian red blood cells with a plasticizer;
freezing said red blood cells; and then
drying said frozen cells to produce said fixed dried mammalian red blood cells.

5. The fixed-dried mammalian red blood cells according to claim 4, having a water soluble polymer covalently coupled to the cell membrane thereof.

6. The fixed-dried mammalian red blood cells according to claim 1, said blood cells further having a water soluble polymer covalently coupled to said cell membrane thereof.

7. A formulation comprising red blood cells according to claim 1 reconstituted in an aqueous carrier solution.

8. The fixed-dried mammalian blood cells of claim 1, wherein said cells are dog cells.

9. The fixed-dried mammalian blood cells of claim 1, wherein said plasticizer is diethylhexylphthalate.

* * * * *